United States Patent [19]

Horrobin

[11] Patent Number: 4,970,076

[45] Date of Patent: Nov. 13, 1990

[54] FATTY ACID COMPOSITION

[75] Inventor: David F. Horrobin, Guildford, England

[73] Assignee: Efamol Holdings PLC, Guildford, England

[21] Appl. No.: 280,410

[22] Filed: Dec. 6, 1988

[30] Foreign Application Priority Data

Dec. 14, 1987 [GB] United Kingdom ................. 8729153

[51] Int. Cl.$^5$ .............................................. A61K 9/64
[52] U.S. Cl. .................................... 424/456; 514/922; 514/885
[58] Field of Search ................. 424/456; 514/922, 885

[56] References Cited

U.S. PATENT DOCUMENTS

| | | | |
|---|---|---|---|
| 4,196,189 | 4/1980 | Raaf et al. | 424/440 |
| 4,554,351 | 11/1985 | Wenger | 546/211 |
| 4,735,965 | 6/1988 | Stenerick et al. | 514/647 |
| 4,822,606 | 4/1989 | Snyderman et al. | 424/88 |

Primary Examiner—Merrell C. Cashion, Jr.
Assistant Examiner—Leon R. Horne
Attorney, Agent, or Firm—Nixon & Vanderhye

[57] ABSTRACT

Composition of a cyclosporin and GLA and DGLA or derivative thereof convertible in the body thereto alone or in a pharmaceutical diluent or carrier.

7 Claims, No Drawings

FATTY ACID COMPOSITION

FIELD OF INVENTION

This invention relates to fatty acid compositions.

GENERAL BACKGROUND

Cyclosporin is an important new drug developed to produce suppression of the immune system in patients receiving organ transplants, such as kidneys, hearts and livers. It is now apparent that it may have much wider uses in conditions such as psoriasis, rheumatoid arthritis, and early diabetes. It is probable but not yet certain that its effectiveness is in those conditions in which the disease process is related to abnormal functioning of part of the immune system.

Cyclosporin is an unusual cyclic peptide containing 11 amino acids. One of these is a nine carbon, olefinically unsaturated compound. Modified cyclosporins also have biological activity, but the olefinic amino acid appears important in this activity. Cyclosporin and its biologically active analogues (the cyclosporin-like compounds) all bind to a family of proteins known as cyclophilins which are found in the thymus gland, lymphocytes and other tissues. Biological activity of the cyclosporins and related compounds appears to be dependent on their ability to bind specifically to cyclophilins.

Unfortunately cyclosporin has a number of side effects, one of which is of particular importance and restricts use of the drug in disease states of only mild to moderate severity. This is that cyclosporin produces impairment of renal function. Although the mechanism of this renal damage is not yet certain, it appears that constriction of blood vessels, so reducing blood flow to the kidney, plays an important part. The mechanism of this vasoconstrictor action is also uncertain but is believed to involve increased production of thromboxane A2, a highly active vasoconstrictor derived from arachidonic acid.

It has been proposed that the renal side effects of cyclosporin may be alleviated by administering the drug in combination with metabolites of alpha-linolenic acid, namely eicosapentaenoic acid (EPA) and docosahexaenoic acid (DHA) which are found in some abundance in fish oils. In animals there is experimental evidence that the treatment can lower the level of thromboxane A2 (TXA2 measured as its metabolite, thromboxane B2) in the kidney, and so reduce vasoconstriction and renal damage.

ESSENTIAL FATTY ACIDS RELATIONSHIPS AND DISCUSSION

There are two series of essential fatty acids (EFAs) which are not inter-convertible in the mammalian body but are related as shown in the following outline of essential fatty acid metabolism:

TABLE 1

| n-6 | n-3 |
|---|---|
| 18:2 delta-9,12 (linoleic acid) | 18:3 delta-9,12,15 (alpha-linolenic acid) |

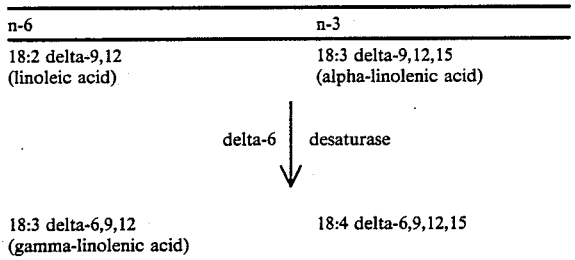

| 18:3 delta-6,9,12 (gamma-linolenic acid) | 18:4 delta-6,9,12,15 |

TABLE 1-continued

| n-6 | n-3 |
|---|---|

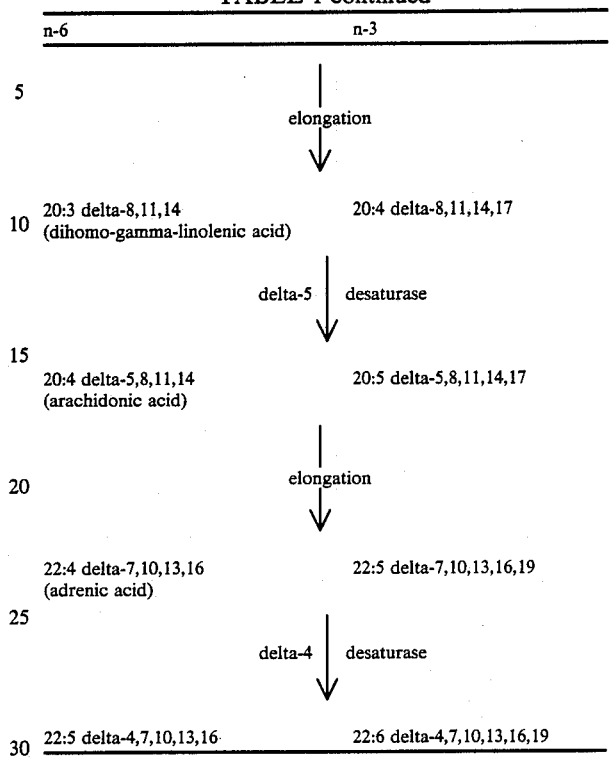

| 20:3 delta-8,11,14 (dihomo-gamma-linolenic acid) | 20:4 delta-8,11,14,17 |
| 20:4 delta-5,8,11,14 (arachidonic acid) | 20:5 delta-5,8,11,14,17 |
| 22:4 delta-7,10,13,16 (adrenic acid) | 22:5 delta-7,10,13,16,19 |
| 22:5 delta-4,7,10,13,16 | 22:6 delta-4,7,10,13,16,19 |

The present invention depends on newly appreciated relationships of cyclosporins with essential fatty acids. As noted above, it has been proposed to ameliorate the adverse effects of cyclosporins by the countervaling effect of the fatty acids found in fish oils on TXA2 levels. However, the fatty acids found in fish oils not only reduce the amount of potentially harmful vasconstrictive thromboxane A2 formed from arachidonic acid, they also reduce the production of vasodilator metabolites such as prostaglandin E1 (PGE1) from DGLA and prostacyclin and PGE2 from arachidonic acid. The fish oil fatty acids, are therefore not the best agents to use in conjunction with cyclosporin, at least when employed alone. DGLA however, and unlike arachidonic acid, produces metabolites which are vasodilator or biologically inert in this regard, and therefore consistently has vasodilator actions. Both DGLA and arachidonic acid are found in some abundance in renal tissue. The vasodilator metabolites of both DGLA and arachidonic acid are believed to be important in the maintenance of normal renal blood flow. Since DGLA has no vasoconstrictor metabolites, it is best to employ an agent which raises levels of DGLA in the kidneys.

While DGLA can be formed from dietary linoleic acid by the pathway shown, the first step in the conversion is extremely slow in humans and in fact rate limiting. Administration of dietary linoleic acid has not been shown to be successful in raising human GLA concentrations: in contrast, by-passing the rate-limiting step by giving GLA, does raise human DGLA levels. In addition to being inherently slow, the formation of GLA is inhibited by a wide variety of factors, including ageing, atopic disorders, diabetes, catecholamines, alcohol, cholesterol, and zinc deficiency.

Administration of GLA or DGLA is an efficient way of raising the concentrations of DGLA in humans. Some of the DGLA is converted to arachidonic acid, but this step is also relatively slow, and the ratio of DGLA to arachidonic acid rises after such administration. Moreover, administration of GLA has been found to inhibit the formation of thromboxane B2 in patients with certain disorders (see Table 2 below). In these studies the GLA was administered in the form of evening primrose oil. The mechanism of inhibition of thromboxane formation is uncertain. However, DGLA can give rise to PGE1, which in turn elevates concentrations of cyclic AMP. Cyclic AMP inhibits the enzyme phospholipase A2 which is known to affect the mobilisation of arachidonic acid from phospholipids and hence the conversion of arachidonic acid to thromboxane and other metabolites.

TABLE 2

| THROMBOXANE B2 PRODUCTION FROM AGGREGATING PLATELETS | | |
|---|---|---|
| ON PLACEBO | ON GLA | |
| Patients with premenstrual syndrome | $186 \pm 44$ ng/ml | $141 \pm 59$ ng/ml | $p < 0.01$ |
| Patients with Raynauld's syndrome | $208 \pm 36$ ng/ml | $179 \pm 18$ ng/ml | $p < 0.05$ |

THE INVENTION

We therefore propose the administration of GLA or DGLA in association (including chemical combination) with cyclosporin and derivatives to counter their side effects, especially the renal side effects. This will be achieved by increasing the formation of vasodilator metabolites from DGLA, and possibly reducing thromboxane formation from arachidonic acid.

Additionally the invention extends to a method of making a medicament for countering the side effects of cyclosporins characterised by the use of the fatty acids as the active medicament together with the method of countering the side effects of cyclosporins characterised by administering such fatty acids to a person suffering from or at risk of such side effects.

The GLA or DGLA may be optionally combined with EPA, 22:5 n-3 and DHA, the fatty acids found in fish oils. These fatty acids will also reduce thromboxane. These fatty acids will, further, increase the ratio of DGLA to arachidonic acid, by inhibiting the enzyme 5-desaturase, which converts DGLA to arachidonic acid.

GLA, DGLA, EPA, 22:5 n-3 and DHA may each be administered in doses of 1 mg to 100 g per day, preferably, 50 mg to 10 g per day. They may be given once per day or in divided doses through the 24-hour period.

Cyclosporin and its related compounds may be administered in doses of 0.1 to 200 mg/kg/day (approx. 5 mg to 15 g/day), preferably 5-20 mg/kg/day (approx. 0.25 to 1.5 g/day).

Both the fatty acids and the cyclosporins may be administered orally or parenterally or by other convenient routes. For use in skin diseases, topical administration may be possible, using preparations of cyclosporin containing 0.1 ng to 100 mg, preferably 0.1 ng to 1 mg per ml, and preparations of fatty acids containing 0.1 ng to 100 mg, preferably 0.1 ng to 10 mg per ml. The fatty acids and cyclosporins may also be administered at different times and by different routes but as cyclosporin is strongly hydrophobic, for topical, and for example for oral and parenteral administration the cyclosporins may conveniently be actually dissolved in the fatty acids.

The term cyclosporins covers not only cyclosporin itself, but any derivative of cyclosporin and compound which has cyclosporin-like activity, shown to be related to cyclosporin by reason of its ability to bind selectively to cyclophilins.

The fatty acids can moreover be administered in the forms of glycerides, salts, esters, amides, or any other pharmaceutically acceptable form which results in a rise in the level of the fatty acid in body tissues by conversion in the body thereto and reference to EFAs herein includes such forms.

Their equivalence is demonstrated by entry into the pathway quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al, page 23, "Analysis of Lipids and Lipoproteins" Ed. Perkins, American Oil Chemists Society, Champaign, Ill., United States of America.

In outline the method is suitably that plasma samples (1 ml) are extracted with chloroform:methanol (2:1). The extract is filtered through sodium sulphate, evaporated to dryness, and taken up in 0.5 ml chloroform:methanol. The lipid fractions are separated by thin layer chromatography or silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% silar on chromosorb WAW 106/230. The carrier gas is helium (30 ml/min). Oven temperature is programmed to rise from 165° C. to 190° C. at 2° C./min. Detector temperature is 220° C. and injector temperature 200° C. Retention times and peak areas are automatically computed by Hewlett-Packard Level 4 integrator. Peaks are identified by comparison with standard fatty acid methyl esters.

PACKS

If it is not desired to have compositions comprising different active materials together, packs may be prepared comprising the materials presented for separate, or part joint and part separate administration in the appropriate relative amounts, and use of such packs is within the purview of this invention.

DIETARY COMPOSITIONS

The invention is chiefly described in terms of methods of treatment and pharmaceutical compositions, but it will be understood that the gamma-linolenic and other acids, being in the nature of dietary supplements, can be incorporated in a dietary margarine or other foodstuffs for use by those taking cyclosporin.

FORMS AND SOURCES OF GAMMA-LINOLENIC AND OTHER ACIDS

Convenient physiologically equivalent derivatives of gamma-linolenic acid and dihomo-gamma-linolenic acid for use according to the invention as with the other acids, includes salts, amides, esters including glyceride esters and alkyl (e.g. $C_1$ to $C_4$) esters, and phospholipids.

If desired, pharmaceutical compositions may be produced for use in the invention by associating the natural or synthetic acids, as such or as derivatives, with an acceptable pharmaceutical vehicle. It is, however, at present convenient to provide at least the gamma-linolenic acid in the form of an available oil having a high gamma-linolenic acid content, hence reference to "oil" herein.

At the present time known natural sources of oils having a high gamma-linolenic acid content are few (there are no known natural sources of significant amounts of dihomo-gamma-linolenic acid). One source of oils currently available is the seed of Evening Primrose species such as *Oenothera biennis L.* and *Oenothera Lamarckiana*, the oil extract therefrom containing gamma-linolenic acid (about 8%) and linoleic acid (about 72%) in the form of their glycerides, together with other glycerides (percentages based on total fatty acids). Other sources of gamma-linolenic acids are Borage species such as *Borago officinalis* which, though current yield per acre is low, provide a richer source of gamma-linolenic acid than Oenothera oil. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

|   |   |
|---|---|
| Palmitate | 6.15 |
| Stearate | 1.6 |
| Oleate | 10.15 |
| Linoleate | 72.6 |
| Gamma-linolenate | 8.9 |

The seed oil extracts referred to above can be used as such or can, for example, if desired, be fractionated to yield an oily composition containing the tri-glycerides of gamma-linolenic and linoleic acids as the main fatty acid components, the gamma-linolenic acid content being, if desired, a major proportion. Seed oil extracts appear to have a stabilising effect upon dihomo-gamma-linolenic acid if present.

SOURCES OF OTHER ACIDS

Natural sources of 22:4 and 22:5 n-6 acids include adrenal glands (22:5) and kidneys (22:4) obtained from slaughter houses, and 22:4 in the fat of the American Snapping Turtle. The n-3 acids are available from fish oils, particularly 20:5 n-3 and 22:6 n-3.

The acids can be isolated from these sources by, for example, saponification under mild non-oxidising conditions followed by preparative gas liquid chromatography. Synthesis of the acids is difficult but not impossible and provides another source.

PHARMACEUTICAL PRESENTATION

The compositions are conveniently in a form suitable for oral, rectal or parenteral administration in a suitable pharmaceutical vehicle, as discussed in detail, for example, in Williams British Patent Specification No. 1,082,624, to which reference may be made, and in any case very well known generally for any particular kind of preparation. Thus, for example, tablets, capsules, ingestible liquid or powder preparations can be prepared as required, and topical preparations also when the gamma-linolenic acid or other acids are absorbed through the skin. Injectable solutions of hydrolysed Oenothera oil may be prepared using albumin to solubilise the free acid.

Advantageously, a preservative is incorporated into the preparation. Alpha-tocopherol in concentration of about 0.1% by weight has been found suitable for the purpose.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

The following examples, made up according to conventional techniques except as to the active ingredients, illustrate the invention in its various forms.

EXAMPLE 1

For oral administration

Soft gelatine capsules containing the following combinations of cyclosporin and fatty acids.

|   | Cyclosporin | GLA | DGLA | EPA | DHA |
|---|---|---|---|---|---|
| A | 30 mg | 200 mg | | | |
| B | 30 mg | 300 mg | | 200 mg | |
| C | 30 mg | 100 mg | 100 mg | 100 mg | 50 mg |
| D | 30 mg | | 300 mg | | |
| E | 100 mg | 400 mg | | | |
| F | 100 mg | 300 mg | | 100 mg | |
| G | 100 mg | 100 mg | 100 mg | 100 mg | 50 mg |
| H | 100 mg | 400 mg | | 200 mg | |

Emulsions containing the above amounts of active ingredients in each 5 ml of emulsion instead of in a capsule.

EXAMPLE 2

For parenteral administration

Sterile ampoules containing the amounts of active ingredients in A to H above in a vegetable oil base.

EXAMPLE 3

For intravenous administration

Emulsions prepared in 5 mol sterile ampoules containing the quantities of active ingredients specified in A to H which can be added to standard solutions of intravenous lipids.

EXAMPLE 4

For topical administration

Ointments and creams made using standard techniques containing active ingredients as follows, by weight:

|   | Cyclosporin | GLA | DGLA | EPA | DHA |
|---|---|---|---|---|---|
| A | 0.01% | 2% | | 0.5% | |
| B | 0.05% | 4% | 1% | 1% | 0.3% |
| C | 0.1% | 5% | | | |
| D | 0.15% | | 2% | | |
| E | 0.1% | | 2% | 1% | |

-continued

|   | Cyclosporin | GLA | DGLA | EPA | DHA |
|---|---|---|---|---|---|
| F | 0.05% | 3% |  | 1% | 0.5% |

I claim:

1. A dosage form of a fatty acid composition alone or in a pharmaceutical diluent or carrier comprising a cyclosporin and a fatty acid selected from the group consisting of GLA, DGLA and a derivative thereof convertible in the body thereto, wherein said fatty acid is in the range of 1 mg to 100 g, and wherein said cyclosporin is in the range of 0.1 ng to 100 mg per ml of said composition.

2. A dosage form of a composition according to claim 1 comprising also an n-3 essential fatty acid selected from the 20:5, 22:5 and 22:6 acids or their derivatives convertible in the body thereto.

3. A method of alleviating the renal side effects of administration of cyclosporin comprising administering a dosage form alone or in a pharmaceutical diluent or carrier to a person in need of same (1) a cyclosporin, and (2) a fatty acid selected from the group consisting of GLA, DGLA and a derivative thereof convertible in the body thereto, together or successively to a person suffering from or at risk of such side effects, wherein said fatty acid is in the range of 1 mg to 100 g, and wherein said cyclosporin is in the range of 0.1 ng to 100 mg per ml of said dosage form.

4. A dosage form of a composition according to claim 1 for administration of 50 mg to 10 g of the or each fatty acid and 250 mg to 1.5 g of the cyclosporin, per day.

5. A dosage form of a composition according to claim 1 comprising 0.1 to 10 mg per ml of the or each fatty acid and 0.1 ng to 1 mg per ml of the cyclosporin.

6. The method according to claim 3, wherein the GLA or DGLA is administered in an amount of 1 mg to 100 g daily and the amount of cyclosporin administered is 5 mg to 15 g daily.

7. The method according to claim 3, wherein the GLA or DGLA is administered in an amount of 50 mg to 10 g daily and the amount of cyclosporing administered is 250 mg to 1.5 g daily.

* * * * *